(12) United States Patent
Morley (10) Patent No.: US 10,709,659 B1
(45) Date of Patent: *Jul. 14, 2020

(54) COMPOSITION AND METHODS FOR HAIR REGROWTH (71) Applicant: Myriam Morley, Westerly, RI (US)

(72) Inventor: Myriam Morley, Westerly, RI (US)

(73) Assignee: NUTRACEUTICAL WELLNESS INC., New York, NY (US)

( * ) Notice: Subject to any disclaimer, the term of this patent is extended or adjusted under 35 U.S.C. 154(b) by 153 days.

This patent is subject to a terminal disclaimer.

(21) Appl. No.: 14/986,525

(22) Filed: Dec. 31, 2015

(51) Int. Cl.
A61K 36/00 (2006.01)
A61K 8/97 (2017.01)
A61K 8/49 (2006.01)
A61K 8/65 (2006.01)
A61K 8/73 (2006.01)
A61Q 7/00 (2006.01)

(52) U.S. Cl.
CPC ............... *A61K 8/97* (2013.01); *A61K 8/498* (2013.01); *A61K 8/4973* (2013.01); *A61K 8/65* (2013.01); *A61K 8/735* (2013.01); *A61Q 7/00* (2013.01); *A61K 2800/20* (2013.01)

(58) Field of Classification Search
CPC ...................................................... A61K 36/00
See application file for complete search history.

(56) References Cited

U.S. PATENT DOCUMENTS

2006/0228426 A1* 10/2006 Cyr .................... A61K 36/18
424/725

FOREIGN PATENT DOCUMENTS

ES 2517741 A1 * 11/2014
GB 2484812 A * 4/2012 ............... A61K 8/19
WO WO 2015099842 7/2015

OTHER PUBLICATIONS

Kalani et al, Ashwagandha root in the treatment of non-classical adrenal hyperplasia. Endocrine Reviews, (Jun. 2012) vol. 33, No. 3, Supp. MeetingAbstracts. Abstract No. MON-488 (Year: 2012).*
Notice of Allowance dated Feb. 11, 2020 in U.S. Appl. No. 15/898,206.
Nutrafol Men, available for sale Feb. 16, 2017, available from Internet, URL: https://nutrafol.com/products/.
Nutrafol Women, available for sale Feb. 16, 2017, available from Internet, URL: https://nutrafol.com/products/.
Office Action dated Oct. 7, 2019 in U.S. Appl. No. 15/898,206.
Restriction Requirement dated Feb. 26, 2019 in U.S. Appl. No. 15/898,206.

* cited by examiner

Primary Examiner — Qiuwen Mi
(74) Attorney, Agent, or Firm — Byrne Poh LLP; Nina R. Horan (57) ABSTRACT The invention provides compositions and methods for promoting hair growth and reducing hair loss using bioactive extracts of curcumin, *Withania somnifera*, and saw palmetto. Tocotrienols, tocopherols, piperine extract, low molecular weight collagen, and hyaluronic acid are optionally included in the compositions and methods.

9 Claims, 3 Drawing Sheets

CATAGEN-INDUCTION

HAIR GROWTH CYCLE DISRUPTION

GROWTH INHIBITION

| Time Elapsed (months) | Composition taken | Range of Avg. Daily Hair Loss | Quality of Hair |
|---|---|---|---|
| 0 | Nothing taken | 200-300 | Wiry, dry, frizzy |
| 1 | 200 mg Curcumin, 5 mg piperine | 200-300 | Wiry, dry, frizzy |
| 2 | 200 mg Curcumin, 5 mg piperine | 150-200 | Wiry, dry, frizzy |
| 3 | 200 mg Curcumin, 5 mg piperine | 100-150 | Hair slightly thicker |
| 4 | 200 mg Curcumin, 5 mg piperine, 250 mg Withania somnifera | 50-100 | Hair attached more strongly at the root (less falls out when pulling gently on handful of scalp hair), new vellus hair growth. |
| 5 | 200 mg Curcumin, 5 mg piperine, 250 mg Withania somnifera, 640 mg Serenoa repens | <50 | Less wiry, smoother, less brittle, significant new growth at the frontal hairline |
| 6 | 200 mg Curcumin, 5 mg piperine, 250 mg Withania somnifera, 640 mg Serenoa repens, 100 mg Tocotrienol/Tocopherol complex | <50 | Hair smoother, much less brittle & frizzy, continuing new vellus hair growth |
| 7 | 200 mg Curcumin, 5 mg piperine, 250 mg Withania somnifera, 640 mg Serenoa repens, 100 mg Tocotrienol/Tocopherol complex, 1000 mg of Hydrolyzed Collagen Types I and III, 100 mg Hyaluronic Acid | <50 | Hair denser and fuller, continuing new hair growth moving the receded frontal hairline further down |

FIGURE 3

COMPOSITION AND METHODS FOR HAIR REGROWTH

Throughout this application various publications are referenced. The disclosures of these publications in their entireties are hereby incorporated by reference into this application in order to more fully describe the state of the art to which this invention pertains.

FIELD OF THE INVENTION

The present invention relates to the field of hair loss, and more particularly to the restoration of hair growth.

BACKGROUND OF THE INVENTION

Hair loss (alopecia) is a widespread problem affecting about 80 million men and women in the United States alone according to the American Academy of Dermatology. The $7 billion hair loss industry is a testament to the significance and the scope of the issue. The most common alopecias are androgenic alopecia, telogen effluvium and alopecia areata.

Androgenic alopecia (AGA) is the most common type of hair loss in both sexes, affecting at least 50% of men by the age of 50 and up to 40% of women in mid-adult life. More recently AGA is being referred to as male pattern hair loss (MPHL) and female pattern hair loss (FPHL) to reflect the differences in clinical presentation and the new science on the pathophysiology of the conditions, which support the modern understanding that hair loss is due to the contribution of other factors, besides androgens and genetic disposition, particularly in FPHL.

In humans, individual hair follicles progress through phases of growth independent of one another. They are subject to and respond individually to the influence of several inductive and inhibitory signaling molecules in the follicle environment. Anagen, the growth phase, generally lasts between 2 to 7 years in a healthy follicle. Catagen is a transitional phase of regression that lasts approximately 2-3 weeks between the growth phase and the resting phase. Telogen, the resting phase, lasts for approximately 3 months. The late stage of telogen is associated with the regeneration of the next growth phase. Loss of coverage, or hair thinning and hair loss, occurs when the normal cycling and growth of numerous follicles are disrupted. The disruption can be widespread, sudden and synchronized causing immediately visible loss or it can be slow, steady and unsynchronized, becoming visible over a long period of time, only when 50% of the follicles have been affected. Hair density and volume decreases when the hair growth cycle is disrupted and more follicles enter catagen and telogen prematurely, while not enough follicles enter anagen to replace them. Further, miniaturization, the signature pathology seen in patients with MPHL & FPHL, can occur where the width of hair fibers progressively decrease in each consecutive cycle causing once thick and long hair fibers to become thinner, lighter, barely visible vellus-like hairs.

A modern view on alopecia describes all hair loss, regardless of its various manifestations and traditional classifications, as the result of a 'disordered hair follicle.' (Breitkopf, T., Dermatol. Clin., 2013, 31(1):1-19). When hair follicles on the scalp are in an unbalanced disordered state, it compromises their function and manifests in hair growth and cycle abnormalities. Different combinations of abnormalities pertain to different disorders. The traditional view held by researchers and clinicians considers hair loss as a disease, which has led to alopecias being classified by their presumed respective causes and/or manifestations. For instance, MPHL/FPHL and telogen effluvium (TE) are classified as non-inflammatory, whereas alopecia areata (AA) and scarring alopecias are classified as inflammatory diseases. Recent findings have begun to challenge this perspective as researchers have found that even in MPHL/FPHL there is significant evidence of micro-inflammation, a term proposed to reflect the indolent inflammatory process in AGA. (Mahe, Y. F., Int. J. Dermatol., 2000, 38(8):576-84). Thus, it is being recognized that in all alopecias there are multiple combinations of factors, like inflammation, that underlie the disordered hair follicle.

The hair growth cycle is primarily maintained through the complex interplay of numerous cytokines, growth factors and transcription factors that signal the cells of the follicles to either induce or prohibit hair growth. These signals are both introduced extrinsically and also produced intrinsically by the follicle's dermal papilla cells (DPCs) that determine follicle and hair fiber characteristics Those extrinsic controls that induce early catagen and inhibit growth, such as the androgen dihydroxytestosterone (DHT), have provided targets for therapies, such as the drug finasteride in the case of DHT. However, even extrinsic factors act on the follicles by altering the production of signaling molecules by the follicle DPCs. The significance of immune signaling and balance in sustaining proper follicle functioning is further underscored by the fact that it represents one of the few sites of 'immune privilege' (IP) in the body. The follicle's IP normally protects the follicle from immune system recognition and inflammatory attack. IP also works to sequester anagen-associated autoantigens within the follicle, protecting them from immune recognition. Studies have shown that the follicle's IP can be compromised by stress-induced neuropeptides such as Substance P (SP) (Peters, E. M., Am. J. Pathol., 2007, 171(6):1872-86) and cytokines such as interferon gamma (IFN-γ). (Xing, L., Nat. Med., 2014, 20(9): 1043-49). Subsequent to this immune system imbalance and collapsed IP, compromised follicles are subject to inflammatory attack. Thus for a follicle to not become 'disordered' and to produce healthy hair, it is vital to maintain an IP.

Inflammatory responses can be further stimulated by the presence of free radicals, also referred to as Reactive Oxygen Species (ROS). ROS are highly reactive molecules with unpaired electrons that can directly damage cellular structures and alter DNA. They are generated endogenously through normal and specific metabolic processes and we are subject to ROS exposure from the environment, for instance in the form of common air pollutants. However, with age, the body's ability to neutralize ROS decreases since production of antioxidant enzymes and endogenous antioxidants decreases with age while ROS generation increases with age resulting in increased oxidative stress on the body, including hair. Compromised hair follicles are known to be particularly vulnerable to ROS from environmental stressors. Further, inflammatory responses, through positive feedback, create a cyclic cascade and generate even more ROS. For example, it has been shown in androgen induced alopecia that the generation of ROS mediates the pro-inflammatory androgen signaling cascade. Similarly, in models of chronic stress, the neurogenic inflammatory pathways of SP were shown to increase ROS and decrease innate antioxidant defenses, leading to hair growth arrest and hair cycle arrest.

Thus, the common underlying pathway of hair loss can be seen as disordered immune signaling and an oxidative imbalance that involve numerous players: pro-inflammatory cytokines, pro-fibrotic and growth inhibiting factors like TGF-β, and inflammatory cells—all perpetuated through chronic generation of free radicals, oxidative stress and further inflammatory changes and immune imbalances. This common pathway in hair loss can be triggered and propagated by several factors including, but not limited to: sudden changes or severe imbalances in nutrition as in crash diets, androgens, genetics, and stress.

Androgens, like other steroid hormones, act on target cells by diffusing through the plasma membrane, binding to specific receptors and then acting on the DNA, inducing the transcription and translation of specific hormone-regulated genes and their products, such as cytokines. In the follicle, testosterone is mostly metabolized by 5α-reductase (5-ar) into DHT. DHT is implicated in the pathogenesis of several androgen responsive disorders such as prostate disease, acne and AGA. It is now recognized that the effects of androgens within follicles are mediated via signaling cascades, which are dysregulated in pathologies like hair loss. The main action of DHT on follicles occurs within the dermal papilla cells, where it binds to androgen receptors, enters the nucleus and leads to increased transcription and overproduction of growth-inhibiting molecules like the cytokine TGF-β that signals catagen induction and apoptosis. Once triggered by minimal amounts of DHT, other factors can maintain the pathophysiology of AGA without the presence of androgens, as seen in men with MPHL who were castrated after puberty. Thus, it appears that blocking androgens alone to combat hair loss is insufficient due to the presence of signaling and dysregulation of the immune balance downstream of the initial insult, triggering a cascade of numerous immune and inflammatory processes that can sustain the alopecic pathway. In fact, androgen-induced overproduction of TGF-β by the DPC's and surrounding fibroblasts also plays a role in perifollicular fibrosis and inflammation—implicated in the pathophysiology of miniaturization in follicles. Of special note, MPHL and FPHL differ in that women have less total 5-ar than men. This may account for why current drug therapies that block 5-ar to treat alopecia produce minimal results in women as compared to men, especially given that systemic DHT and 5-ar are generally within normal limits in women with FPHL.

Stress has long been disputed as playing a measurable role in hair loss. Recent research, however, has begun to examine the roles of psycho-emotional stress, nerves and immune cells in hair growth and has discovered new pathways that link the central nervous system with the hair follicle. New evidence provides definable neurological, neuroendocrine and immunological mechanisms through which stress can inhibit hair growth. Psycho-emotional stress results in systemic elevation of nerve growth factor, a key modulator of hair growth termination, and substance P (SP), the prototypic stress-associated neuropeptide that is widely acknowledged as a potent modulator of immune responses and neurogenic inflammation of the skin. In addition to compromising follicle IP, elevated levels of SP induce the proliferation and degranulation of local mast cells and these mast cells in turn release a host of pro-inflammatory mediators like histamine and cytokines like TNF-α. The resulting neurogenic inflammation has been shown to cause hair growth arrest and promotion of follicle regression. The follicle has also been shown to be highly sensitive to stress hormones like cortisol, which are known to cause catagen induction, and the follicle even contains all the needed machinery to self-produce these hormones. Specifically, one of the major stress hormones, corticotropin-releasing hormone (CRH), is elevated systemically during stress and can bind to the follicle, which induces the follicle to produce even more CRH and cortisol.

There are limited options regarding pharmaceutical therapeutics for the treatment of AGA in the United States, and only one is indicated for FPHL. One therapeutic, is minoxidil. While minoxidil's mechanism of action has not been clarified despite its use since 1988 in the treatment of AGA, it is widely believed to elongate the anagen phase by acting on potassium channels in the hair follicle, thereby improving follicular circulation. Some known side effects of minoxidil are dizziness, chest pain, difficulty breathing and swelling. The topical version has the further side effects of causing rashes and skin irritations in some users. The other FDA-approved therapeutic, finasteride, is only indicated in MPHL. It works by competitively binding the enzyme 5-ar, thereby reducing the conversion of testosterone into DHT, which is a known androgen trigger for hair loss. Finasteride is FDA-approved for treatment of AGA only in men and has also been reported to cause side effects of erectile dysfunction, ejaculatory dysfunction and loss of libido in a segment of users.

The complexity of the hair loss pathway requires a multi-pronged approach to treat the most prominent aspects of the problem. Pharmaceutical therapies such as minoxidil and finasteride achieve some success in treating hair loss, but ultimately only address single elements of a larger problem, not addressing downstream dysregulated signaling or the common pathway of inflammation and oxidative stress. Additionally, they are associated with potential significant and debilitating side effects. There is a need for a therapy which in addition to addressing just one trigger, like androgens, also addresses the disordered immune signaling of catagen-inducing cytokines and addresses the inflammation that is both a result and a promoter of the disordered signaling. An ideal therapeutic should further address the generation and effect of ROS in hair loss due to the role of oxidative stress in aggravating inflammation. And, importantly, there is a need for a therapy which can also address psycho-emotional stress and its effects on hair loss. Finally, there is a need for a therapy that is safe and does not induce similar side effects.

Nutraceutical formulations and the multi-targeting bioactive properties of certain plant phytonutrients offer a possible solution since they can target multiple triggers of hair loss at once. Further, the fact that these phytonutrients are natural in origin and known to be safe for consumption avoids many of the concerns of undesired side effects, which are common with pharmaceuticals.

One such phytonutrient is curcumin (diferuloyl methane) which is found in the rhizome of the turmeric plant, *Curcuma longa*, and is readily extracted from the plant, U.S. Pat. No. 5,861,415. Curcumin has been shown to slow hair loss by down-regulating expression of the DHT-binding Androgen Receptor, inhibit type II 5-ar, support regrowth by decreasing levels of the catagen-signaling cytokine TGF-β and to be a potent antioxidant and anti-inflammatory agent. (Pumthong, G., J. Dermatolog. Treat., 2012, 23(5):385-92). It has significant activity against pro-inflammatory cytokines like TNF-a and IL-1, both known to signal catagen and to inhibit follicle growth. Curcumin's anti-stress and neuroprotective properties have been studied extensively and one neurotransmitter it inhibits is Substance P, which in high levels has been shown to compromise the follicle's immune privilege and to induce mast cell degranulation that leads to catagen, hair growth inhibition and increased inflammation. As for its safety profile, curcumin has not been shown to evidence toxicity in human studies at doses of up to 8000 mg daily for three months. (Cheng, A. L., Anticancer. Res., 2001, 21(4B):2895-2900).

Another phytonutrient is *Withania somnifera*, commonly known as Ashwagandha. It is a medicinal plant that has been employed for centuries in ayurvedic medicine and has recently been observed to reduce hair loss. (Kalani, A., BMJ Case Rep., 2012). Ashwagandha has also been recognized as an adaptogen, a unique class of herbal ingredients that result in the restoration of normal physiological function (homeostasis), and to increase the body's resistance to the effects of stress, such as by decreasing cellular sensitivity to stress. Ashwagandha is known to rebalance and lower the levels of the stress hormone cortisol, to improve thyroid function, and to elevate the body's endogenous antioxidant enzymes through its principal withanolides. Ashwagandha also exhibits inhibitory effects on pro-inflammatory cytokines such as IL-6 and TNF-α. The active compounds in *Withania somnifera* leaves and roots are $C_{28}$ steroidal lactone molecules known as withanolides, such as Withaferin A, and are extracted from the plant using known methods, U.S. Pat. No. 7,108,870.

Extracts of *Serenoa repens* or "saw palmetto," a dwarf palm tree, have been observed to help hair regrowth in male pattern baldness. (Chittur, S., Evid. Based Complement Alternat. Med., 2011:985345). The saw palmetto berry contains over 100 known compounds. The active ingredients in saw palmetto are contained in the purified lipid soluble extract of the saw palmetto berry. This has been found to contain 85 to 95 percent fatty acids (predominantly lauric, caprylic, and caproic), long chain alcohols, and sterols (including beta-sitosterol, stigmasterol, cycloartenol, lupeol, lupenone, and methylcycloartenol). Saw palmetto naturally inhibits the activity of the testosterone catalyzing 5-ar enzyme, but unlike the drug finasteride it does not interfere with Prostate Specific Antigen levels. In comparative studies with finasteride, saw palmetto was even associated with an improvement of sexual dysfunction. (Suter, A., Phytother. Res., 2013, 27(2):218-26). The berries also contain high molecular weight polysaccharides (sugars), which may reduce inflammation or strengthen the immune system.

Tocotrienols, together with tocopherols, which are members of the Vitamin E family, possess potent antioxidant activity by directly neutralizing reactive oxygen species and also raising the body's own antioxidants and antioxidant enzymes. Tocotrienols have also been shown to provide protection against UV light and oxidative stress and to promote hair regrowth in humans. (Beoy, L. A., Trop. Life Sci. Res., 2010, 21(2):91-99). A natural source rich in tocotrienols and tocopherols is palm oil, with crude palm oil (also referred to as the "tocotrienol-rich fraction") containing up to 800 mg/kg weight of α- and γ-tocotrienol isotypes. The distribution of vitamin E in palm oil is 30% tocopherols and 70% tocotrienols. Natural sources of vitamin E, such as palm oil, are believed to have greater bioactivity than synthetically manufactured vitamin E.

Piperine, the active principle of the dried, unripe fruits of various black pepper plants, is an alkaloid which has been shown in in vitro studies to protect against oxidative damage by inhibiting or quenching free radicals and reactive oxygen species. It has also been shown to enhance the bioavailability of a number of therapeutic drugs and phytonutrients like curcumin by strongly inhibiting hepatic and intestinal aryl hydrocarbon hydroxylase and UDP-glucuronyl transferase. (Srinivasan, K., Crit. Rev. Food Sci. Nutri., 2007, 47(8): 735-48). In addition to possessing antioxidant properties, piperine has further been shown to possess analgesic and anti-inflammatory properties in animal studies. (Tasleem, F., Asian Pac. J. Trop. Med., 2014, 7S1:S461-8).

It is an object of the present invention to provide a nutraceutical supplement composition that simultaneously inhibits the molecular triggers of hair loss associated with stress and androgens and further addresses the concurrent cascade of disordered cytokine signaling, inflammation and oxidative damage that is brought on by their activity, thereby preventing damage and shrinkage to hair follicles and promoting more follicles to enter a healthy hair cycle in a multi-targeted, comprehensive manner.

SUMMARY OF THE INVENTION

Accordingly, the present invention provides a composition for promoting hair growth and reducing hair loss, comprising from 100 to 1000 mg of an extract of *Curcuma longa*, from 100 mg to 1000 mg of an extract of the roots and leaves of *Withania somnifera*, and at least 200 mg of saw palmetto extract. Advantageously, the composition further comprises from 100 mg to 1000 mg of tocotrienols and tocopherols. The composition may further comprise low molecular weight collagen and hyaluronic acid and the collagen may be Type I and Type III collagen and have a molecular weight of less than 5000 daltons. The collagen may be present in an amount from 500 mg to 2000 mg, and said hyaluronic acid may be present in an amount from 100 mg to 1000 mg.

The composition of the invention may further include at least 200 mg of curcumin, at least 100 mg of withanolides, at least 200 mg of saw palmetto extract, and at least 100 mg of tocotrienols and tocopherols comprising a complex of 78% tocotrienols and 22% tocopherols, at least 1000 mg of Type I and III collagen having a molecular weight of less than 3000 Daltons, and at least 100 mg of hyaluronic acid.

The composition of the invention may further include at least 5 mg of piperine.

The composition of the invention may further include one or more compounds from the group consisting of green tea extract, L-methionine, L-cysteine hydrochloride, resveratrol, capsaicin, biotin, selenium, Vitamin D, Vitamin A, and Vitamin C.

The invention provides a food item comprising the composition of the invention, and a mixture of additional components selected from the group consisting of vitamins, amino acids, minerals, proteins, carbohydrates, fats, flours, flavoring, and sweetener.

The invention also provides a method of promoting hair growth and reducing hair loss by administering to a subject an effective amount of the composition of the invention, in a pharmaceutically suitable vehicle, for a time sufficient to promote hair regrowth and reduce hair loss in subjects exhibiting symptoms of alopecia.

Additional features, advantages, and aspects of the present disclosure are set forth or apparent from consideration of the following detailed description, drawings, and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the present disclosure, are incorporated in and constitute a part of this specification, illustrate aspects of the present disclosure and, together with the detailed description, serve to explain the principles of the present disclosure. In the drawings.

DETAILED DESCRIPTION OF THE INVENTION

The present invention provides novel nutraceutical compositions which have been shown to reduce hair loss and promote the growth of new hair in individuals suffering from various types and degrees of hair loss. Current treatments for hair loss and promotion of hair growth fall under two categories: a) pharmacological or b) nutrient supplements. Pharmacological treatments come with the risk of significant side effects and nutrient supplements only provide nutrition while ignoring the ongoing causes of the actual hair loss itself. A non-pharmacological nutraceutical formulation such as the current invention provides a much needed option for those who suffer hair loss, since it both addresses the underlying causes of hair loss using natural remedies without pharmacological side effects and provides the nutrition needed for improved hair growth. It can further be used as both a preventative and as a complementary therapy to augment pharmacological treatments.

Figure 1:
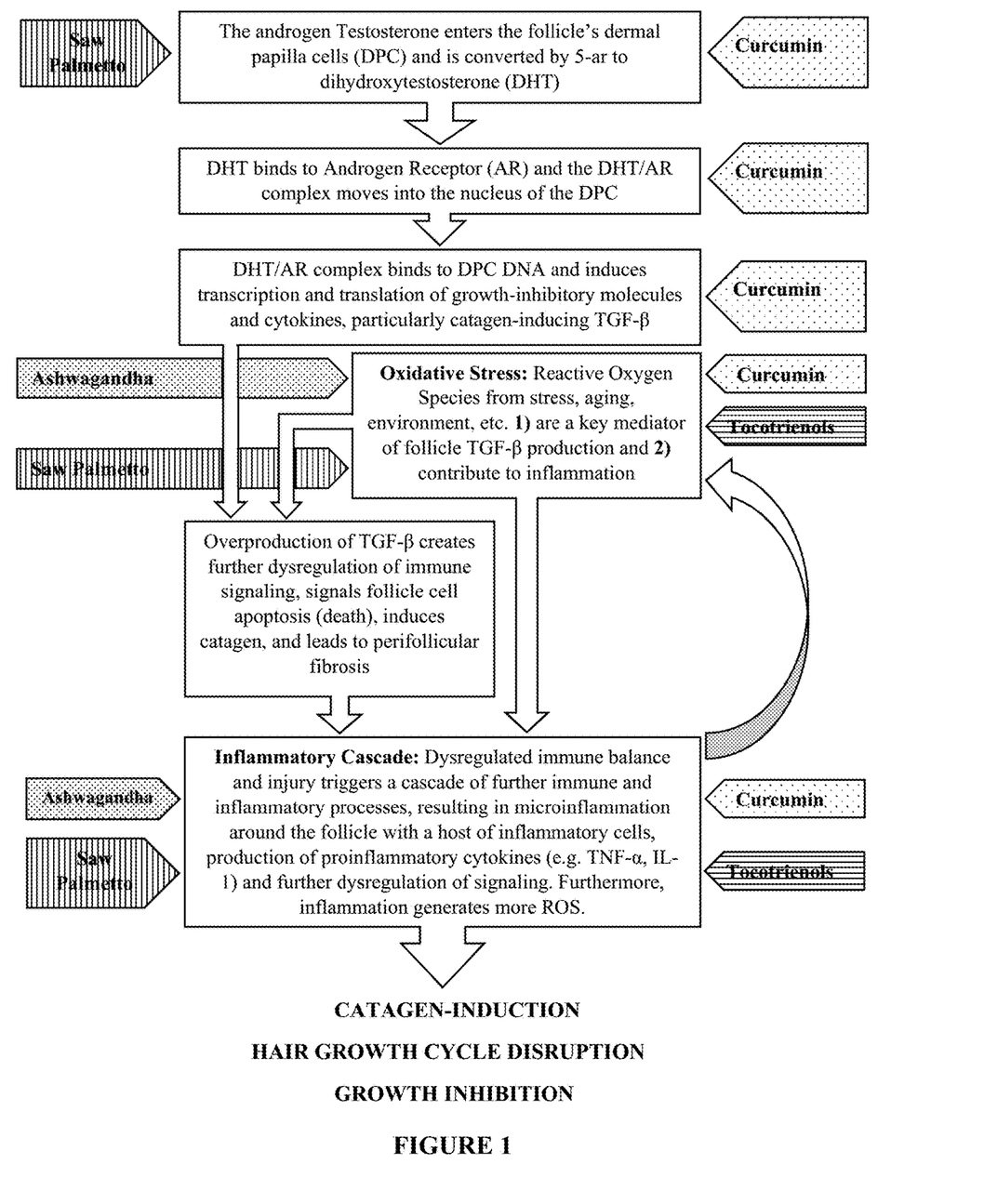
FIG. 1 depicts the androgen pathway and indicates where components of the invention help mitigate damage to hair follicles.
Figure 2:
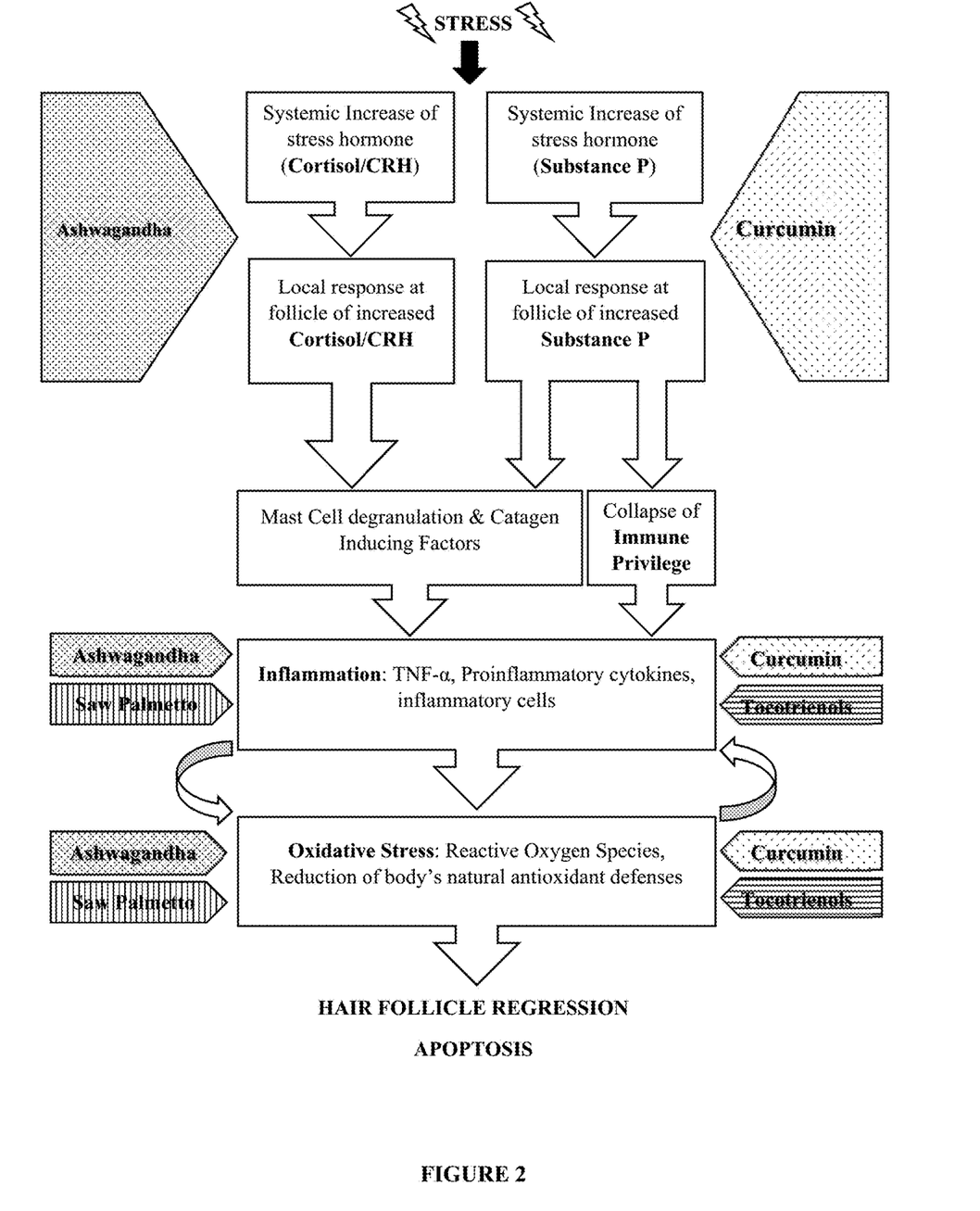
FIG. 2 depicts how the stress pathway may lead to hair loss and indicates where components of the invention help mitigate damage to hair follicles.

The present invention provides compositions and methods for promoting hair health and hair growth. Without being bound by any particular theory or explanation, the novel nutraceutical compositions of the invention contain components which may synergistically inhibit multiple triggers of hair loss such as DHT (See FIG. 1) and the stress hormone cortisol (See FIG. 2); reduce inflammation and oxidative stress associated with the self-sustaining common pathway of hair loss; and provide necessary nutrition which may be better absorbed and utilized by hair follicles after the follicles are rebalanced by the other components of the compositions of the invention.

In one implementation of the invention for promoting hair growth and reducing hair loss, the composition comprises curcumin, ashwagandha, and saw palmetto.

In a preferred embodiment for male subjects, the composition includes at least 200 mg of curcumin, at least 100 mg of withanolides, and at least 500 mg of bioactive saw palmetto, preferably standardized to contain at least 85% fatty acids and sterols.

In another preferred embodiment for hair regrowth and to reduce hair loss in female subjects, the composition of the invention further includes at least 200 mg of bioactive saw palmetto extract, preferably standardized to contain at least 85% fatty acids and sterols. This embodiment containing less saw palmetto is preferred in women due to the fact that women typically have 5 times less total testosterone than men. The same benefits can be achieved with less of this DHT inhibitor since women have less testosterone which can be metabolized into DHT.

In a more preferred embodiment of the aforementioned compositions, the compositions can additionally contain one or more of an effective amount of an extract from saw palmetto, tocotrienols, tocopherols, piperine, low molecular weight collagen, and hyaluronic acid.

The said saw palmetto extract is preferably a bioactive extract of the *Serenoa repens* plant. Methods for obtaining the bioactive components of the invention are known, for example, by extraction of plant materials, as described in U.S. Pat. No. 6,039,950. The components can further be obtained with increased bioactivity and/or bioavailability, using known methods for improving the bioavailability of bioactive components extracted from plants, resulting in the need for less of the bioactive component as described in U.S. Pat. Nos. 8,329,233, 6,153,198, and 5,891,465). The bioactive saw palmetto extract is further preferably standardized to contain at least 85% fatty acids and sterols.

The tocotrienols and tocopherols for use in the compositions of the invention may be combined in a complex containing 78% tocotrienols and 22% tocopherols by weight.

The said low molecular weight collagen is preferably hydrolyzed Type I and Type III collagen having a molecular weight of less than 3000 daltons.

Thus, an implementation of a composition of the invention may include at least 200 mg of curcumin, at least 100 mg of withanolides, at least 500 mg of bioactive saw palmetto, preferably standardized to contain at least 85% fatty acids and sterols, and one or more of the following: at least 200 mg of saw palmetto extract, 10 mg to 1000 mg of tocotrienol and 50 mg to 1000 mg of tocopherols present in a complex comprised of 78% tocotrienols and 22% tocopherols, at least 5 mg of piperine, 500 mg to 2000 mg of hydrolyzed Types I and III collagen having a molecular weight of less than 3000 daltons, and/or 100 mg to 1000 mg of hyaluronic acid.

For female subjects an implementation of a composition of the invention may contain at least 200 mg of curcumin, at least 100 mg of withanolides, and at least 200 mg of bioactive saw palmetto, preferably standardized to contain at least 85% fatty acids and sterols, and one or more of the following: at least 200 mg of saw palmetto extract, 10 mg to 1000 mg of tocotrienol and 50 mg to 1000 mg of tocopherols present in a complex comprised of 78% tocotrienols and 22% tocopherols, at least 5 mg of piperine, 500 mg to 2000 mg of hydrolyzed Types I and III collagen having a molecular weight of less than 3000 daltons, and/or 100 mg to 1000 mg of hyaluronic acid.

The compositions of the invention may also include one or more of the following ingredients: green tea extract, L-methionine, L-cysteine hydrochloride, resveratrol, capsaicin, biotin, selenium, Vitamin D, Vitamin A, and/or Vitamin C.

The invention further provides a method of promoting hair growth and reducing hair loss in a subject experiencing hair loss of the scalp, by administering to the subject an effective amount (e.g. an amount effective to promote hair regrowth, slow the progression of hair loss, etc.) of said composition comprising at least 200 mg of curcumin, at least 100 mg of withanolides, and at least 200 mg of bioactive saw palmetto, preferably standardized to contain at least 85% fatty acids and sterols, and one or more of the following: at least 200 mg of saw palmetto extract, 10 mg to 1000 mg of tocotrienol and 50 mg to 1000 mg of tocopherols present in a complex comprised of 78% tocotrienols and 22% tocopherols, at least 5 mg of piperine, 500 mg to 2000 mg of hydrolyzed Types I and III collagen having a molecular weight of less than 3000 daltons, and/or 100 mg to 1000 mg of hyaluronic acid.

The compositions and method of the invention for alleviating hair loss, may be effective to improve hair loss caused by, for example, forms of alopecia including androgenetic alopecia, alopecia areata, alopecia mucinosa, telogen effluvium, chronic inflammation, extreme and/or chronic stress, diabetes, cellulitis, hair treatments, hereditary disorders, hormonal changes, hyperthyroidism, hypothyroidism, malnutrition, lupus, medication side effects, including from chemotherapy and birth control, radiation, aging and trichotillomania.

In an implementation, the invention provides methods for the treatment and/or reduction of hair loss in a subject, comprising administering to the subject in a pharmaceutically suitable vehicle, an effective amount of a composition of the invention comprising at least 200 mg of curcumin, at least 100 mg of withanolides, and at least 200 mg of bioactive saw palmetto, preferably standardized to contain at least 85% fatty acids and sterols, and one or more of the following: at least 200 mg of saw palmetto extract, 10 mg to 1000 mg of tocotrienol and 50 mg to 1000 mg of tocopherols present in a complex comprised of 78% tocotrienols and 22% tocopherols, at least 5 mg of piperine, 500 mg to 2000 mg of hydrolyzed Types I and III collagen having a molecular weight of less than 3000 daltons, and/or 100 mg to 1000 mg of hyaluronic acid. The compositions can additionally include further amounts of nutrients necessary and beneficial hair growth which are known to those having ordinary skills in the art.

"Pharmaceutically suitable vehicle" as used herein refers to a non-toxic solid, semisolid (also referred to as "softgel") or liquid filler, diluent, encapsulating material or formulation auxiliary of any type, suitable for the particular route of administration and desired release rate (e.g. immediate or controlled release) of the active compounds, and are well known in the art. Pharmaceutically suitable vehicles and excipients that may be used to formulate oral dosage forms are described in the Handbook of Pharmaceutical Excipients, American Pharmaceutical Association, Arthur H. Kibbe (2000), incorporated herein by reference in its entirety.

The bioactive compounds in the compositions of the invention may be combined in a single dosage form or for unit-dose or multi-dose administration. The compositions can be formulated into suitable preparations for administration to a subject, such as solutions, suspensions, tablets, dispersible tablets, capsules, powders, sustained release, for oral administration or in sterile solutions or suspensions for parenteral administration, as well as transdermal patch preparation, nasal formulation and dry powder inhalers et al. The compositions may also be formulated as liquid dosage forms such as elixir, suspension or syrup. The compositions are formulated into compositions using techniques and procedures well known in the art.

Dosage of the therapeutic agent(s) of the invention is dependent upon many factors including, but not limited to, the severity of the hair loss, the subject's age, general health and individual response to the compositions of the invention. Accordingly, dosages of the compositions can vary and be readily adjusted, depending on each subject's response.

In one implementation of the invention, the compositions of the invention may be administered to a subject in an amount of at least approximately 1800 mg per day as a single dose, or may be divided into two or more dosages administered throughout a 24 hour period. Ingesting at mealtimes may improve absorption of some of the components of the compositions of the invention. The time of day the given dose or fraction of the given dose is administered can vary by day. The compositions of the invention may be taken on a daily basis until desired hair growth is achieved, or indefinitely.

In addition to oral dosage forms, the compositions of the invention may be incorporated with other ingredients into food, for example by adding the compositions to mixtures used to prepare a "food bar," cookie, cake or other edible item. Mixtures of ingredients for preparing nutrition bars and other baked and non-baked items are known. Flavoring and sweetener may be added to mask any "medicine taste" of the compositions of the invention. Preservatives may be added to improve shelf life.

In accordance with the practice of the invention, the subject may be a human. The subject may also be a mammal, such as a monkey, ape, dog, cat, cow, pig, horse, sheep, rabbit, mouse, rat or a bird.

The person of ordinary skill in the art will recognize that additional ingredients can be used in the compositions and methods of the present invention, for example to promote hair health and appearance, while maintaining effectiveness or enhancing the activity of the compositions in promoting hair growth and reducing hair loss.

Example 1

The male subject was a 49-year old male. He began to notice mild hair thinning at the age of 28. However, the hair loss became significantly more pronounced after he underwent radiation therapy for thyroid cancer at the age of 32. Over the next 17 years, he went to numerous physicians and took the only FDA-approved pharmaceuticals for hair loss (minoxidil and finasteride) but the improvement was minimal and didn't stall his progression to Stage III Vertex/Stage IV MPHL on the Hamilton-Norwood scale. During this time he also tried several natural supplements and topical formulations, but did not see any noticeable improvement. Prior to taking the implementations of the invention described herein, he had taken *Serenoa repens* alone and biotin alone, which did not result in a noticeable cessation of hair loss or new hair growth. In 2012 he was additionally diagnosed with Rheumatoid Arthritis (RA), which is an autoimmune condition that creates a pro-inflammatory state in the body and significantly affects joints. The subject was also suffering from chronic stress at this time. The subject notes that as a result of his condition his hair loss and the quality of his hair also worsened.

Figure 3:
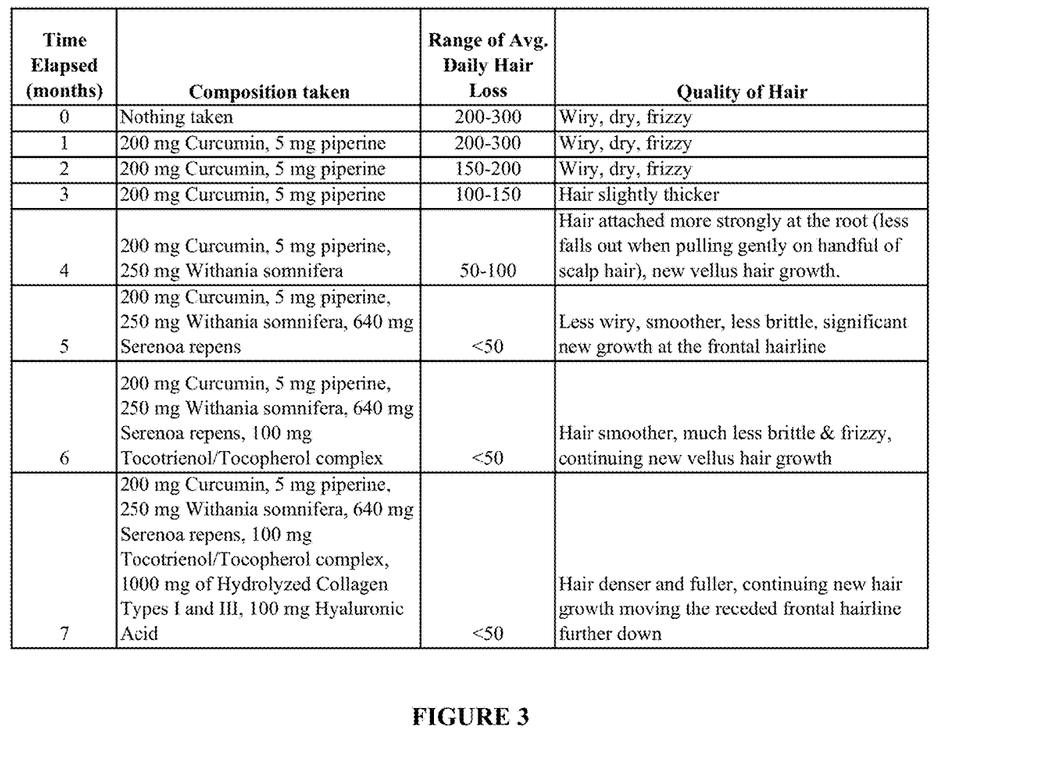
FIG. 3 is a table depicting the subject's results of various implementations of the invention over a 7-month period.

The subject was first given Curcumin extracted from *Curcuma Longa* standardized to 95% Curcuminoids including: curcumin, desmethoxy curcumin, bis-desmethoxy curcumin and volatile oils of turmeric rhizome (BCM-95®, Dolcas-Biotech, LLC, Chester, N.J.) in amounts of at least 200 mg a day. To improve curcumin absorption and bioavailability, it was taken together with 5 mg of standardized extraction of piperine. After continuing this regimen for 3 months and in addition to improvement of his RA symptoms, he noted decreased hair shedding and slightly improved hair thickness and quality. During month 4, the subject was additionally given a daily 250 mg dose of Ashwagandha extracted from *Withania somnifera*, containing at least 8% withanolide glycosides and 32% oligosaccharides from the roots and leaves (Sensoril®, Natreon, New Brunswick, N.J.) for stress associated with his condition and work. He noted that month that there was a further decrease in his hair loss and some small growth of new hairs. During month 5, the subject was additionally given a daily dose of Certified Organic saw palmetto extract Standardized 85-95% fatty acids (Valensa Eustis, Fla.) in the amount of 640 mg a day. During that month he experienced significant new growth at the frontal hairline and temples, a decrease in hair loss and improvement in hair quality. During month 6, the subject added a 100 mg dose of tocotrienol/tocopherol complex comprising 78% tocotrienols and 22% tocopherols (Tocomax™ 20%, Carotech, Malaysia) a day. This addition lead to further improvement in new hair growth at the hairline and the vertex and his hair became less brittle and smoother. Lastly, in month 7, He was additionally given approximately 1000 mg of hydrolyzed marine collagen Types I and III (Youtheory, Tustin, Calif.) and 100 mg of hyaluronic acid (NOW Foods, Bloomingdale, Ill.). At the end of month 7 the subject reported improvement in hair density, thickness, and continued new hair growth. The subject's progression is tabulated in FIG. 3.

Before initiation of the experiment, the subject had a bald spot on his crown covering an area of approximately 78 $cm^2$. Upon evaluation after 7 months, the results showed that the progression of his hair loss and the recession of the frontal hairline were stalled. There was also notable and measurable new growth at the hairline, temples and vertex. The original bald spot had been reduced to an area of approximately 38 $cm^2$, or an increase of hair growth of approximately 40 $cm^2$. Further, there was increase in the thickness and overall quality of hair.

After having significant loss of scalp hair for a period of 17 years, the subject experienced significant new hair growth and overall increase in thickness of scalp hair. The subject experienced no noticeable side effects from consumption of the composition.

Example 2

The subject, a 36 year-old male with early stages of MPHL (stage II on the Hamilton-Norwood scale), began taking an implementation of the invention consisting of 200 mg curcumin, 5 mg of piperine, 250 mg of withanolides, 640 mg of *Serenoa repens,* 100 mg Tocotrienol/Tocopherol complex comprising 78% tocotrienols and 22% tocopherols, 900 mg of Hydrolyzed Collagen Types I and III, 100 mg Hyaluronic Acid, 5 mg Vitamin A, 3 mg Vitamin D, 60 mg Vitamin C, 0.2 mg Selenium, 3 mg Biotin, 5 mg Capsaicin, 50 mg Resveratrol, 100 mg L-Methionine and 100 mg L-Cysteine Hydrochloride. After 6 months of daily ingestion the composition, he not only noticed a halt to the progression of his alopecia, but he also noted new hair growth, especially in the front—filling in his receding hairline. His hair also became thicker and more manageable. His wife and colleagues noted the increased hair growth and thickness. He even decided to start growing his hair longer. Overall, he also noted that he was feeling overall much healthier and even experienced increased libido.

Example 3

The subject was a 51 year-old female with moderate to severe stage 2 (Ludwig scale) manifesting in typical female pattern hair loss—significant widening of the part, diffuse hair loss and thinning of the crown. She started noticing hair thinning and loss in her 20's and tried many different products, without improvement. She concurrently suffered from chronic stress. The subject began taking began taking an implementation of the invention consisting of 200 mg curcumin, 5 mg of piperine, 250 mg of withanolides, 200 mg of *Serenoa repens,* 100 mg Tocotrienol/Tocopherol complex comprising 78% tocotrienols and 22% tocopherols, 900 mg of Hydrolyzed Collagen Types I and III, 100 mg Hyaluronic Acid, 5 mg Vitamin A, 3 mg Vitamin D, 60 mg Vitamin C, 0.2 mg Selenium, 3 mg Biotin, 5 mg Capsaicin, 50 mg Resveratrol, 100 mg L-Methionine and 100 mg L-Cysteine Hydrochloride daily. After a 6 month period, she saw dramatic improvement not only in quality and shine, but also saw significant hair growth within 7 months of use.

Advantages of the Invention

The compositions of the invention thus produced significant and visible benefits in mitigating hair loss and promoted new hair growth.

While the present disclosure has been described in terms of exemplary aspects, those skilled in the art will recognize that the present disclosure can be practiced with modifications in the spirit and scope of the appended claims. These examples and embodiments given above are merely illustrative and are not meant to be an exhaustive list of all possible designs, aspects, applications or modifications of the present disclosure.

What is claimed is:

1. A composition for promoting hair growth and reducing hair loss, comprising from 100 to 1000 mg of an extract of *Curcuma longa*, from 100 mg to 1000 mg of an extract of the roots and leaves of *Withania somnifera*, at least 200 mg of saw palmetto extract, low molecular weight collagen, hyaluronic acid and a pharmaceutically suitable encapsulating material.

2. The composition of claim 1, further comprising from 100 m to 1000 mg of tocotrienols and tocopherols.

3. The composition of claim 1, where said collagen is Type I and Type III collagen and has a molecular weight of less than 5000 daltons.

4. The composition of claim 1, wherein said collagen is present in an amount from 500 mg to 2000 mg, and said hyaluronic acid is present in an amount from 100 mg to 1000 mg.

5. A composition for promoting hair growth and reducing hair loss, comprising at least 200 mg of curcumin, at least 100 mg of withanolides, at least 200 mg of saw palmetto extract, at least 100 mg of tocotrienols and tocopherols comprising a complex of 78% tocotrienols and 22% tocopherols, at least 1000 mg of Type I and III collagen having a molecular weight of less than 3000 Daltons, at least 100 mg of hyaluronic acid and a pharmaceutically suitable encapsulating material.

6. A composition for promoting hair growth and reducing hair loss, comprising from 100 to 1000 mg of an extract of *Curcuma longa*, from 100 mg to 1000 mg of an extract of the roots and leaves of *Withania somnifera*, at least 200 mg of saw palmetto extract, at least 5 mg of piperine and a pharmaceutically suitable encapsulating material.

7. The composition of any one of claim 1, 5 or 6, further comprising one or more compounds selected from the group consisting of green tea extract, L-methionine, L-cysteine hydrochloride, resveratrol, capsaicin, biotin, selenium, Vitamin D, Vitamin A, and Vitamin C.

8. A food item comprising the composition of any one of claim 1, 5 or 6, and a mixture of additional components selected from the group consisting of vitamins, amino acids, minerals, proteins, carbohydrates, fats, flours, flavoring, and sweetener.

9. A method of promoting hair growth and reducing hair loss comprising administering to a subject exhibiting symptoms of alopecia an effective amount of the composition of claim 1 for a time sufficient to promote hair regrowth and reduce hair loss.

* * * * *

UNITED STATES PATENT AND TRADEMARK OFFICE
CERTIFICATE OF CORRECTION

PATENT NO. : 10,709,659 B1  
APPLICATION NO. : 14/986525  
DATED : July 14, 2020  
INVENTOR(S) : Myriam Morley et al.

It is certified that error appears in the above-identified patent and that said Letters Patent is hereby corrected as shown below:

On the Title Page

Item (12) delete "Morley" and insert -- Morley et al. --.

Item (72) In the Inventor list, the following two inventors should be added: Roland Peralta, New York, NY (US) and Giorgos Tsetis, New York, NY (US).

Signed and Sealed this  
Thirty-first Day of December, 2024

Derrick Brent  
*Acting Director of the United States Patent and Trademark Office*